United States Patent
Mattsson et al.

(10) Patent No.: US 8,758,423 B2
(45) Date of Patent: Jun. 24, 2014

(54) DEVICE AND METHOD FOR TREATING RUPTURED ANEURYSMS

(75) Inventors: Erney Mattsson, Västra Frölunda (SE); Torbjörn Lundh, Billdal (SE)

(73) Assignee: Graftcraft I Goteborg AB, Billdal (SE)

( * ) Notice: Subject to any disclaimer, the term of this patent is extended or adjusted under 35 U.S.C. 154(b) by 1195 days.

(21) Appl. No.: 12/457,664

(22) Filed: Jun. 18, 2009

(65) Prior Publication Data

US 2010/0324649 A1 Dec. 23, 2010

(51) Int. Cl.
*A61F 2/06* (2013.01)

(52) U.S. Cl.
USPC .......................................................... 623/1.11

(58) Field of Classification Search
CPC ................................................ A61F 2002/077
USPC .................. 606/191, 192, 200; 623/1.11–1.12
See application file for complete search history.

(56) References Cited

U.S. PATENT DOCUMENTS

| | | | |
|---|---|---|---|
| 5,693,088 A | 12/1997 | Lazarus | |
| 7,252,680 B2 | 8/2007 | Freitag | |
| 7,862,601 B2 * | 1/2011 | Sanati et al. | 623/1.11 |
| 2004/0116996 A1 | 6/2004 | Freitag | |
| 2004/0193245 A1 | 9/2004 | Deem et al. | |
| 2005/0033416 A1 | 2/2005 | Seguin et al. | |
| 2005/0080480 A1 * | 4/2005 | Bolea et al. | 623/1.15 |
| 2006/0212112 A1 | 9/2006 | Evans et al. | |
| 2007/0156228 A1 | 7/2007 | Majercak et al. | |
| 2007/0162106 A1 * | 7/2007 | Evans et al. | 623/1.23 |
| 2007/0282423 A1 | 12/2007 | DiCarlo | |
| 2008/0071287 A1 | 3/2008 | Goto | |

FOREIGN PATENT DOCUMENTS

| | | |
|---|---|---|
| WO | WO 97/19653 | 6/1997 |
| WO | WO 98/41167 | 9/1998 |
| WO | WO 02/083037 | 10/2002 |
| WO | WO 2004/004603 | 1/2004 |
| WO | WO 2004/037116 | 5/2004 |

OTHER PUBLICATIONS

International Search Report dated Aug. 24, 2009 for corresponding International Application No. PCT/EP2009/057586.

* cited by examiner

*Primary Examiner* — Darwin Erezo
*Assistant Examiner* — Kendra Obu
(74) *Attorney, Agent, or Firm* — Harness, Dickey & Pierce, P.L.C.

(57) ABSTRACT

A stent device for treating an aneurysm is disclosed. The stent device comprises an expandable balloon with a channel extending through said balloon from one side to another, and a supporting stent connected to said balloon. In an operative disposition, when the expandable balloon is expanded, the supporting stent is arranged at least partly within said channel of said expandable balloon. Further, the supporting stent has walls which are permeable to blood. The stent device may be introduced and removed by endoscopic procedures, with a relatively simple procedure. Thus, the stent device is highly useable for fast and temporary treatment of ruptured aneurysms.

15 Claims, 12 Drawing Sheets

DEVICE AND METHOD FOR TREATING RUPTURED ANEURYSMS

FIELD OF THE INVENTION

The present invention relates to a stent device and a kit for treating aneurysms.

BACKGROUND OF THE INVENTION

Arteries can have a pathological dilatation called aneurysms. The most common location for an aneurysm is in the aorta just below the take off of the renal arteries. It occurs in approximately 5% of the population above the age of 60 years. About 75% of the aortic aneurysms are asymptomatic and are found unexpectedly. An aortic aneurysm can rupture, which is a life-threatening condition because of extensive blood loss into the abdominal cavity. The risk for rupture increases with size. The rupture is most commonly located at the lower left part of the aneurysm. Approximately 80% of the patients facing a rupture die immediately. Those who reach a hospital have a chance of survival averaging 45%.

The optimal initial treatment for a patient with a ruptured aortic aneurysm would theoretically be to first substitute for the losses of blood and other essential body fluids and optimize basic functions such as the cardiopulmonary and renal capacities. The risk for re-bleeding and immediate death is unfortunately so big that there is no time to finalize such undertakings. There are two different interventions available today. One in which the abdominal cavity is opened and the ruptured part of the aorta is replaced with an artificial graft. This is a major operation and the traditional method.

An alternative treatment is to exclude the aneurysm with an endovascular procedure. An artificial graft is placed within the aneurysmal sac which excludes the aneurysm from the blood flow and pressure and thereby stop further blood loss. The graft is inserted through the femoral arteries in the groins. This intervention is less traumatic but needs x-ray investigations to measure the optimal dimensions of various parts of the graft to be implanted since that vary considerably between individuals. These investigations take time. Furthermore, the proximal control above the bleeding point is achieved through a balloon, which is applied adjacent to the renal arteries. This blockage will influence the renal circulation and eventually also the circulation to visceral organs with potential serious consequences to follow.

Known prostheses for use in such interventions are e.g. disclosed in US2005033416, US 2007156228, US 2007282423, WO 2004/004603, US 2004/0193245, WO 97/19653 and WO 98/41167.

Both the above-discussed types of interventions can only be performed in hospitals of considerable size with extensive services.

Consequently, the current methods of treating aneurysms have disadvantages including too little time to execute an optimal treatment, which often leads to fatal consequences for the patient. For example optimally, there is a need for time of transport of severely sick patients to suitable hospitals, time to substitute and optimize patients before any type of intervention and time for necessary x-ray interventions and measurements to find a suitable endovascular graft.

Furthermore the traditional practice does not follow the proven principles for improved survival in connection to sudden big physical and physiological traumas. These principles can be described in the following two steps: i) damage control with minimal interventions and ii) delayed final repair.

There is therefore a need for a device and method that enables a faster and less traumatic procedure to take care of the immediate life-threatening condition.

SUMMARY OF THE INVENTION

It is therefore an object of the present invention to provide a device, kit and method enabling a procedure which alleviates the above-discussed problems of the prior art.

This object is achieved with a device, kit and a method according to the appended claims.

According to a first aspect of the present invention there is provided a stent device for treating an aneurysm comprising: an expandable balloon with a channel extending through said balloon from one side to another; and a supporting stent connected to said balloon, and in an operative disposition, when the expandable balloon is expanded, arranged at least partly within said channel of said expandable balloon, wherein said supporting stent has walls which are permeable to blood. In the operative disposition, the supporting stent is preferably arranged to extend over essentially the whole channel of the expandable balloon, and also preferably arranged to extend outside said channel.

This stent device is relatively straightforward to introduce into an aneurysm, making the medical procedure fast. Further, the stent device is useable for essentially all patients and on aneurysms of any size and location. Consequently, pre-procedural measurements and adaptations are not necessary. Thus, the new stent device may be used to quickly obtain a reliable coverage of the site of rupture of the aneurysm by means of the expandable balloon. At the same time, the channel in combination with the supporting stent provides a fluid communication through the aneurysmal area, thereby allowing for sufficient blood flow distal to the location of the aneurysm. Hereby, the stent device can be used to alleviate the acute condition of the patient, and remain in place for a sufficient time to prepare for a more complicated medical procedure, such as arrangement of an artificial replacement graft with an endovascular intervention or an open operation. Thus, time is hereby provided to allow e.g. transport to an adequate hospital for a more complicated subsequent procedure, measurement and planning in preparation for a subsequent procedure, and time to prepare and stabilize the patient for the subsequent intervention.

Thus, the present invention is consistent with the above-discussed principles of treatment of sudden serious physical and physiological traumas described in the two steps: damage control with minimal intervention and delayed final repair.

Thus, the new stent device provides means for quickly achieving a temporary solution which provides ample time to adequately prepare for a more permanent solution. The stent device can remain in place during a time period ranging from a few hours to some days, or even a week or more, depending on e.g. the state of the patient. It is envisaged that the new stent device will normally be used for about 24-48 hours.

With the new stent device, the expandable balloon can be inflated to temporarily cover the rupture of e.g. an aortic aneurysm. The stent device has a channel, preferably centrally arranged within the balloon, with a permeable supporting stent, such as a spiral-stent, which will secure the blood flow to distal branches. The stent device is very compact during delivery, and by e.g. positioning the balloon and the supporting stent in line in a delivery-sheath the diameter of the device will be reduced during insertion. Hereby, the stent device is insertable through a relatively limited opening.

The stent device can e.g. be inserted through the femoral arteries in the groins as an endovascular procedure. When the stent device has reached its preferred destination in the aneurysm, the balloon is expanded to the size needed. Since the device is not dependent on the configuration or size of the aneurysm, the principle "one size fits all" can be applied, which excludes the need for measurements before insertion.

Due to the flexibility and configuration of the expandable balloon, the process can in a preferable embodiment be reversed by e.g. deflating the balloon in a controlled manner while unisonly pulling the central scaffolding in order to retrive the provisional device to be replaced by a permanent solution.

Thus, the stent device is easy and quick to apply and to remove, and it fits anyone. The device can be used at any hospital and will give the necessary time for transportation, time for medically optimizing the patient and time for x-ray investigations. Furthermore, it will follow the known principles for better survival in connection to life-threatening situations; damage control with a minimal intervention and delayed final repair. Thus, the present device may decrease the risk for severe or fatal consequences for patients with ruptured aneurysms. At the final position the balloon will protect from further bleeding by coverage of the rupture site. This position will be maintained in an adequate position and the maintaining may be further supported e.g. by having an upper surface profile of the balloon which presses the balloon distally and laterally. The distal mechanical movement will be further enhanced by having a stent with a smaller diameter than the diameter of the adjacent non-aneurysmal aorta. This will act as a pressure-reducer with a higher blood pressure above than below the device, forcing it downwards.

Preferably, the relative position between the expandable balloon and the supporting stent in an axial direction of the stent device is variable, and wherein in an insertion disposition, the expandable balloon and the supporting stent are arranged in line with each other. However, it is also possible to arrange the balloon, in the insertion disposition, within the supporting stent, or alternatively outside the supporting stent. In particular, this latter alternative would be feasible when the supporting stent has a variable diameter, since it would then still be possible to obtain a compact and thin device for insertion.

The diameter of the stent device, in a collapsed disposition, is preferably significantly smaller than the original size of the blood vessel in which the aneurysm has occurred, and also significantly smaller than the size of the blood vessel in which the stent device is to be introduced and removed during the endovascular insertion and extraction procedures.

Further, the balloon is preferably connected to the supporting stent only at or adjacent to a proximal end of said supporting stent. Hereby, the expandable balloon may in an insertion disposition be arranged within or in line with the supporting stent, and being eversible into an expanded state outside said supporting stent in the operative disposition. However, other ways of making the balloon and the supporting stent displaceable in relation to each other are also feasible. Preferably, the balloon is also made of a relatively thin expandable material.

In one embodiment, the connection of the supporting stent to the balloon is only at the top of the stent. This is equal to that the upper luminal entrance of the stent, will function as a pressure reducing part. With the balloon inflated this provides a preferably central channel with a bigger diameter than the stent below its upper luminal entrance. The balloon will have a tendency to move and expand laterally—away from the stent. Since the stent is permeable, blood flow distally will not have a risk for severe mechanical obstruction through the device in its aortic position. The blood flow to the legs is further secured by the extension of the stent into one of the iliac arteries. The distal outflow through the device will thereby be optimally positioned in connection to the aortic bifurcation.

Further, the connection or integration of the stent in the upper surface of the balloon will support the shape of the surface of the balloon. This surface may, as discussed above, enhance the movement of the balloon downwards and laterally towards the rupture site. At removal this connection/integration will after the deflation of the balloon facilitate the docking of the balloon into an extraction sheath, e.g. by pulling at distal threads connected to the stent device. The stent and the balloon may hereby be docked in line, with the balloon on the top. The principal steps to have a device firmly packed, expanded in a working position and shrinked to make it removable through an endovascular approach is thereby achieved.

Hereby, it becomes possible to arrange the balloon and the stent in a very compact state, with a very narrow diameter, for insertion, which makes the insertion easy.

Further, the expandable balloon preferably has a torus shape in an expanded state. This will support its function to cover the site of rupture. The lower end of the channel through the balloon should preferably be concave, or funnel-shaped, to secure the blood flow to the arteries below. Additionally or alternatively, the upper end may also be concave, further improving the flow conditions and the fixation of the balloon. Such a surface will together with the blood flow, force the balloon downwards and outwards.

The balloon preferably comprises parts with a wall material of different thickness and/or flexibility, arranged to provide the desired shape when inflated. For example, the walls of the balloon may have a constitution that provides a balloon with a tendency to first expand outwards during inflation, and which provides a concave, funnel-like appearance of the end portions close to the channel.

The supporting stent preferably has a variable diameter, said diameter being remotely controllable, making it possible to reduce the diameter from a distance. The supporting stent is also preferably self expandable, whereby it automatically strives to resume an expanded state after being released from a compressed state. Hereby, the supporting stent will e.g. automatically become larger when released from a compressed state within the delivery sheath.

Further, the supporting stent can preferably be formed of threads arranged in at least two interfoliated spirals. The term "threads" is in this application to be construed broadly, to cover any thread-like structure, such as thin bands, filaments, twinned wires and the like in many different possible materials such as various metals or plastics. In this case, the ends of the threads forming the spirals preferably extend beyond the supporting stent, whereby variation in the tension of these extending thread ends provides the remote controllability of the diameter of the supporting stent. Hereby, these threads can be positioned through the vascular access and on the patient's external surface. When the device needs to be explanted, pulling of the threads will reduce the diameter of the spiral-stent making also the removal easy. However, other ways of obtaining a controllably variable diameter are also feasible. Further, it is also possible to use a supporting stent with a fixed diameter.

Thread ends of the threads forming the stent will preferably extend beyond the tube-like form of the stent, and out through the entry site of the arterial system of the patient, positioned on the skin of the patient. Hereby, the thread ends may be pulled for control of the diameter of stent. Furthermore, the thread ends make it possible at removal to apply a docking sheath around these threads already outside the vascular tree. The sheath can be advanced to a position where the stent has its form of a tube and when pulling at the external thread ends the tube will reduce its diameter and the docking sheath can slide in the space between the inflated balloon and the stent in the aorta until it reaches the upper connection between the stent and the balloon.

The permeable supporting stent, such as the above-discussed spiral-stent, will secure the blood flow to subsequent (downstream) arteries, such as the arteries to both legs of the patient. The spiral-stent will expand to a predetermined size when the stent device has been inserted into the aneurysm. However, it is also possible to use a supporting stent with a fixed diameter.

The supporting stent (or several supporting stents) will preferably extend into one of the outflow arteries to secure the position of the stent device in relation to these arteries. The supporting stent is preferably only connected to the balloon at its top, where it can be intergraded to the upper surface of the balloon to support the shape of this surface and to facilitate removal of the balloon. The lack of connection between the supporting stent and the balloon along the main body of the supporting stent facilitates flow of blood to the other arteries, in which it does not extend. The lack of connection between the supporting stent and the balloon along the main body of the supporting stent is also advantageous to get a sheath in place for removal.

The spirals in the supporting stent when made of spirals are preferably positioned opposite each other at all locations in their tubular formation. The threads forming the spirals preferably extend beyond the tubular part into a standard straight configuration. Pulling these straight threads will make the spiral-stent longer and simultaneously reduce its diameter thereby increases also the space between the inflated balloon and the spiral-stent. Both motions are advantageous when removing the stent device with e.g. a sheath. The anti-force to the pulling of the threads can e.g. be provided by the inflated balloon, or by an anchored guide wire.

The diameter of the supporting stent in the operative disposition is preferably smaller than the original diameter of the blood vessel in which the aneurysm has occurred. Thus, the diameter of the supporting stent is preferably smaller than a normal aorta (i.e. less than 2 cm). Through the reduction in diameter the blood pressure will be higher above the channel than below it. This will force the whole stent device downwards, to secure its position where most ruptures occur and improve perfusion of proximal organs necessary for a persistent life. The small diameter will also be advantageous for providing a thin device during insertion.

The distal mechanical movement of the stent device will also be further enhanced by having a stent with a smaller diameter than the blood vessel (typically the aorta) where it is placed. This will act as a pressure-reducer with a higher blood pressure above than below the device—forcing it downwards. Another advantage with the difference in diameters between the aorta and the device is that the reduced circulating blood volume will mainly be distributed above the renal arteries—to organs necessary to keep the patient alive in his threatening condition. These organs are the viscera in the abdominal cavity, the kidneys, the heart and the brain. The priority will be given in front of circulation to the legs. However the circulation to the legs will still be more than sufficient as long as the patient is lying in a bed.

Further, the expandable balloon preferably has a length in the axial direction of the stent device which is shorter, and preferably significantly shorter, than the length of the aneurysm. In particular, it is preferred that the length of the balloon is dimensioned not to threaten the flow to the renal arteries when arranged in the active position, and also not so long that it makes the device unsuitable for aneurysms with longer necks. Hereby, the balloon covers the main distance between the renal arteries to the aortic bifurcation.

According to another aspect of the present invention there is provided a kit for treating an aneurysm comprising: a delivery sheath; and a stent device of the type discussed in the foregoing; wherein the delivery sheath releasably accommodates the stent device. The stent device will be released from the delivery sheath at its working position.

Hereby, similar advantages as discussed above in relation to the first aspect of the invention are obtained.

Preferably, the balloon is connected to the supporting stent at one end and to the delivery sheath at an opposite end. Further, the connection between the balloon and the delivery sheath is preferably releasable.

Thus, the balloon and the supporting stent may initially be positioned in line in the delivery-sheath to reduce the diameter of the device during insertion. This will provide a very narrow diameter, and make the insertion much easier. The balloon will e.g. be present at the upper end of the delivery sheath and the supporting stent below. The balloon will hereby preferably be connected to the top of the delivery sheath so it can be everted over the supporting stent when the delivery sheath is pulled backwards. The top of the delivery sheath preferably has markers possible to see under e.g. fluoroscopic vision. A pusher may also be present at the lower end of the supporting stent in the delivery sheath to be used as an anti-force when the delivery sheath is pulled back. A channel for inflation of the balloon and the straight extension of the metal threads connected to the supporting stent may extend through the end of the delivery sheath.

The connection between the delivery sheath and the stent device, and in particular between the delivery sheath and the balloon, is preferably releasable, which makes it possible to separate the delivery sheath after insertion. One possible alternative is that the connection is strong against pulling forces but weak against torsion, which makes it possible to release the delivery sheath by means of twisting. Another alternative to releasing the connection between the delivery sheath and the balloon is e.g. to have parts held together with a thread that can be pulled away to break the connection.

Further, at least one, and preferably both, the stent device and the delivery sheath may comprise markers visible by external observation, such as by means of fluoroscopic vision. Preferably, such marks are arranged at the top and bottom of the supporting stent, to ensure perfect position. Additionally or alternatively, there can be provided a marker between the top and the bottom. This middle marker will preferably be located at a distance from the top of the spiral-stent, which is equal to the length of the balloon. The latter example of middle marker is particularly useful when the stent has a length making it suitable to be extended into one of the arteries to the leg.

The kit preferably also comprises an extraction sheath for removal of the stent device. The extraction sheath is preferably arranged to be inserted into the aneurysm, and to admit for the stent device to be collapsed therein. For example, the supporting stent may be self-expandable and is in one setting formed with threads in a spiral-antispiral formation. The thread ends may in one configuration extend beyond the tubular formation of the supporting stent. By pulling in these extended thread ends the diameter of the supporting stent will be reduced, making it possible to remove the stent device from the aneurysm. Thereafter, it may e.g. be replaced by a permanent solution by an endovascular procedure. The removal will in one embodiment include the docking of the stent and connected balloon in a removal sheath similar to the delivery sheath.

According to still another aspect of the present invention, there is provided a method for treating an aneurysm, comprising the steps of: inserting a kit of the above-discussed type into the aneurysm; pulling back the delivery sheath, thereby releasing the stent device; and expanding the expandable balloon in the aneurysm, wherein a fluid communication through the aneurysm is created through the channel in the balloon.

Hereby, similar advantages as discussed in the foregoing in relation to the other aspects of the invention are obtained.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DESCRIPTION OF PREFERRED EMBODIMENTS

Figure 1:
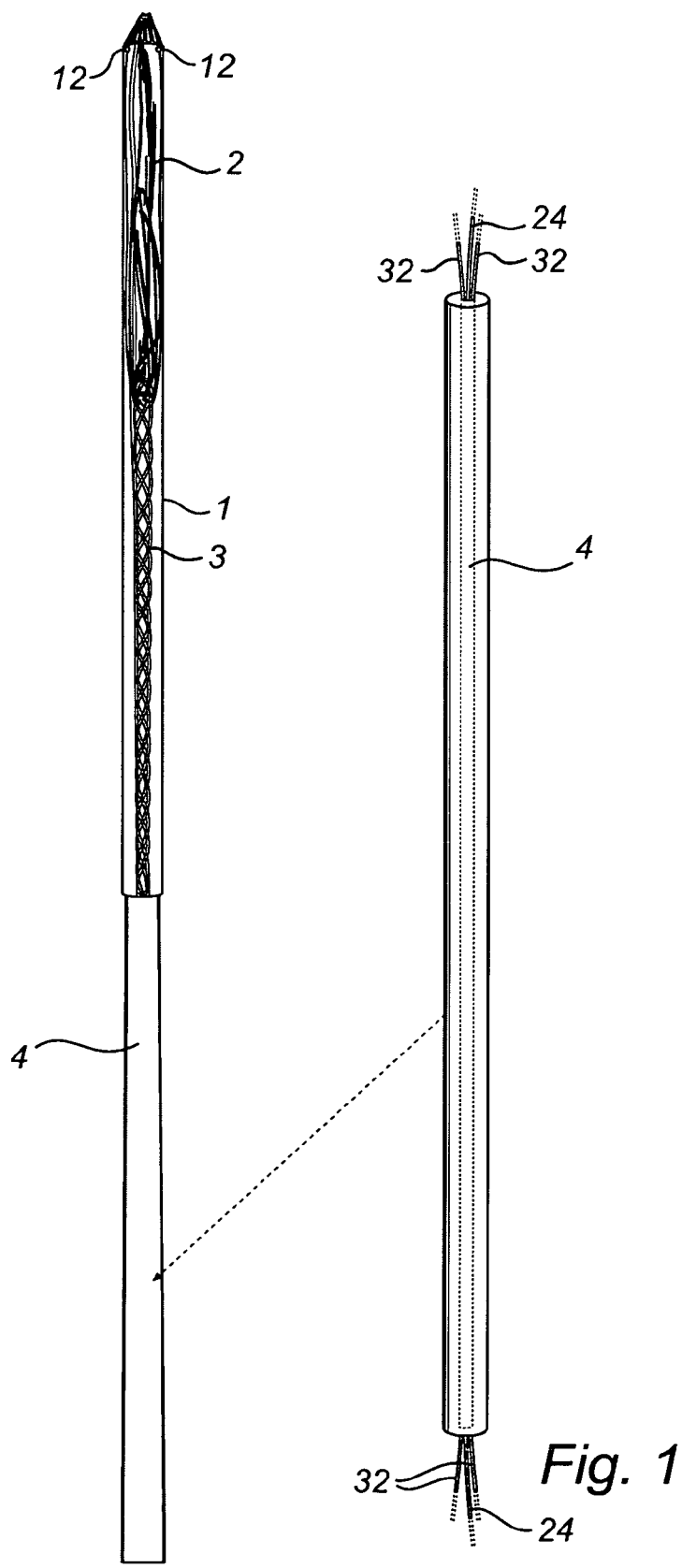
FIG. 1 is a schematic overview of a kit including a stent device according to one embodiment of the present invention, in a compact insertion disposition.
Figure 1A:
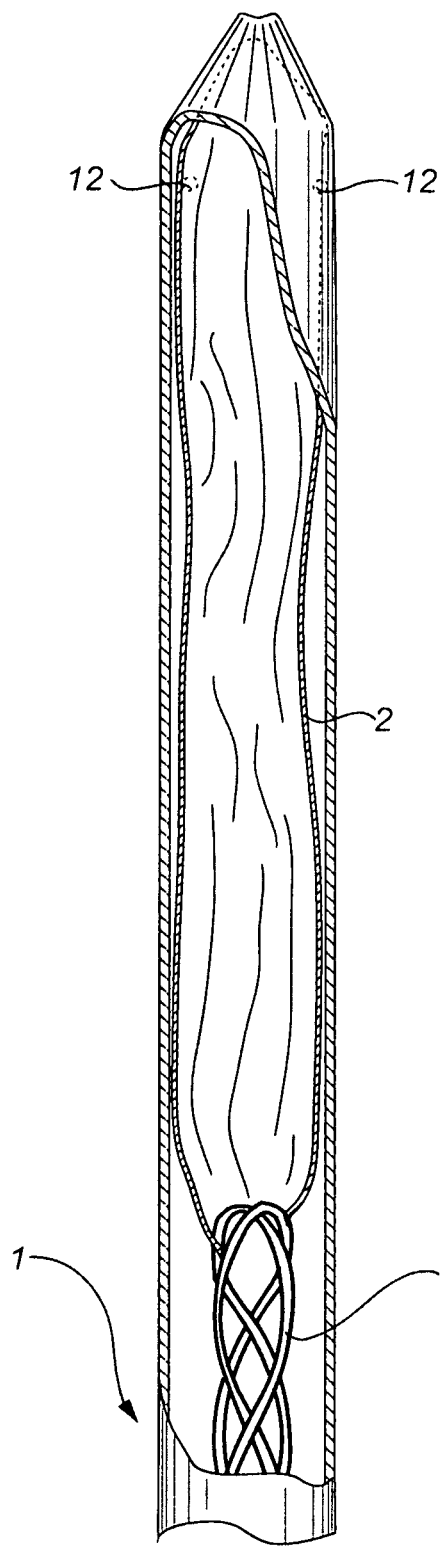
FIG. 1a is an exploded tip view of the stent as illustrated in FIG. 1.
Figure 2:
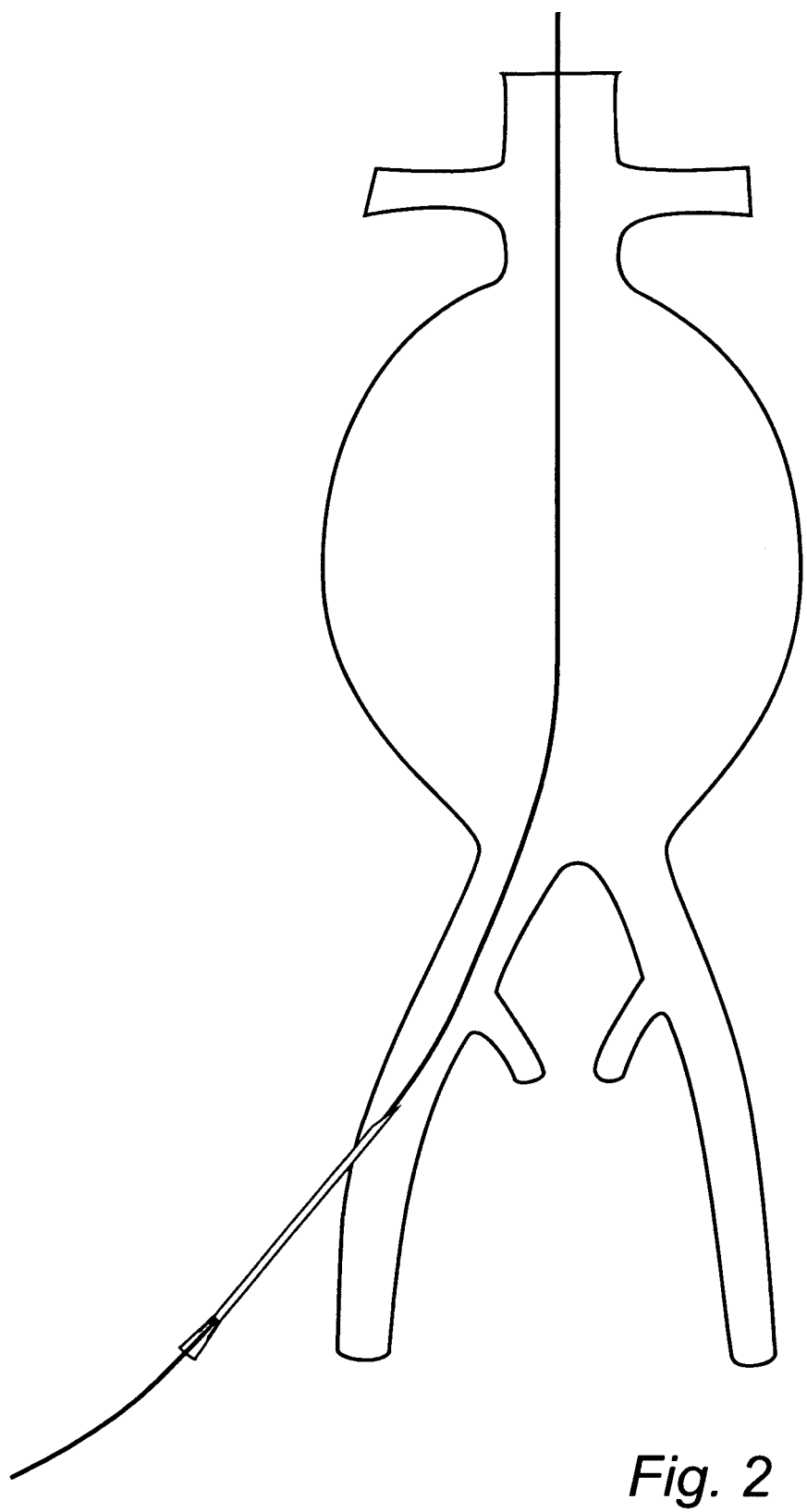
FIGS. 2-7 illustrate different steps when inserting the stent device of FIG. 1 into an operative disposition.
Figure 3:
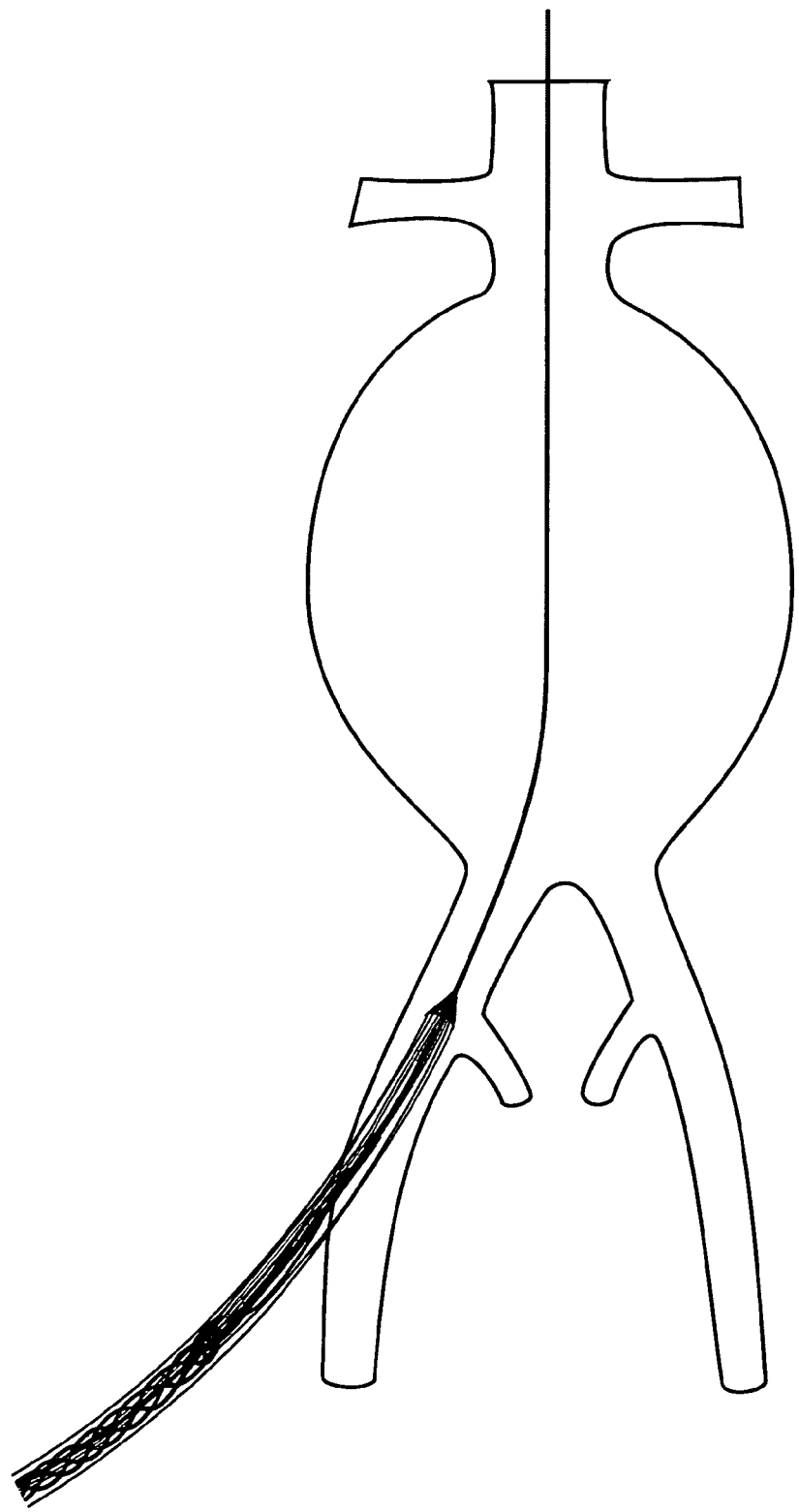

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

With reference to FIG. 1, a kit according to an embodiment of the invention includes a stent device as schematically illustrated. The kit comprises a delivery sheath 1, which accommodates a balloon 2 in a compact state, arranged at the proximal end of the delivery sheath, and formed into a rounded tip portion. Below the balloon 2, and connected to the balloon, is a supporting stent 3. Further, a pushing rod or insertion shaft 4 is arranged displaceable inside the delivery sheat. The pushing rod 4 will be present at the lower, distal end of the supporting stent 3 in the delivery sheath 1 to be used as an anti-force when the delivery sheath is pulled back.

The delivery sheath 1 is preferably made of plastic material. The arrangement of the balloon and the supporting stent in line in the delivery-sheath provides a very small diameter of the device during insertion. The balloon is preferably connected to the top of the delivery sheath, by means of a connection 13 (see also FIG. 4), so it can be everted over the supporting stent (see below) when the delivery sheath is pulled backwards (see also FIG. 4-6). The top of the delivery sheath preferably has markers 12 possible to see under fluoroscopic vision.

Figure 7:
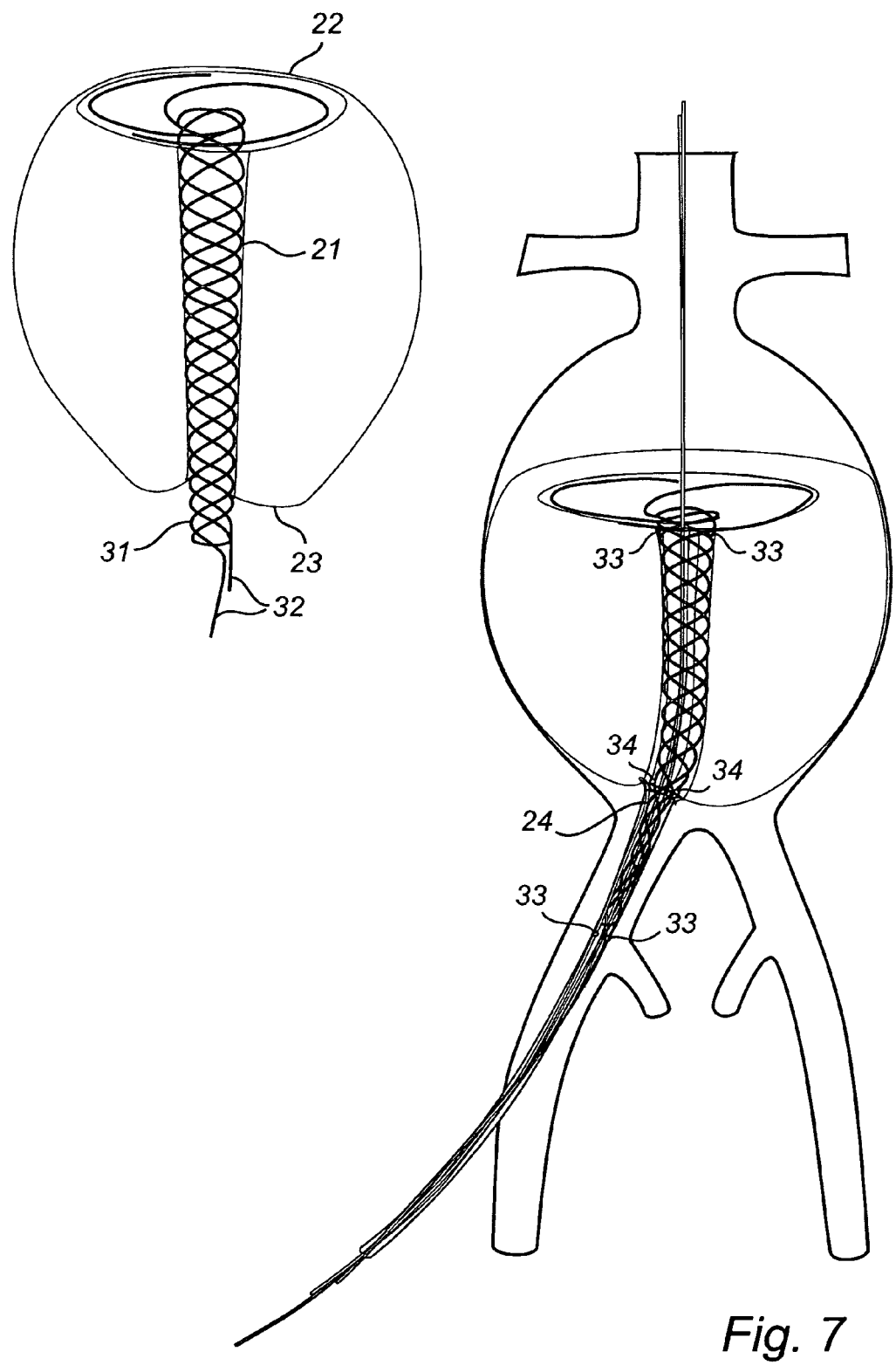

As best seen in e.g. FIG. 7, the balloon comprises a channel 21 extending through said balloon from one side 22 to another side 23. Preferably, the channel is arranged centrally in the balloon. Further, a thin tubing 24 forming a channel for inflation of the balloon is preferably extended to the end of the delivery sheath.

The balloon is preferably torus-shaped and thin enough to be well packed. The balloon is preferably connected to the top of the delivery sheath. The connection site of the balloon to the delivery sheath will later be at the lower end of the stent device after evertion (see below). The connection between the balloon and the delivery sheath is preferably possible to release. One possible alternative is that the connection is strong against pulling forces but weak against torsion. Another alternative is to pull away a thread, which initially keeps the parts together inducing the release.

The supporting stent 3 is connected to the balloon, and is, in an operative disposition, when the expandable balloon and the stent are expanded, arranged at least partly within the channel 21 of the balloon. Further, the supporting stent has walls which are permeable to blood.

The supporting stent 3 is preferably formed of two or more spirals 31, curled interfoliated in different direction. The spirals 31 in the spiral-stent are preferably positioned opposite each other at all locations in their tubular formation. The supporting stent will expand to a predetermined size when the delivery sheath is pulled back. The spirals are preferably made of metal threads, and also, the threads forming the spiral-stent preferably extends beyond the tubular part into control ends 32 of a standard straight configuration. These control ends 32 can be positioned through the artery and on the patient's external surface. The threads forming the spirals are extended beyond the tubular part into a standard straight configuration. Pulling of these straight threads will make the spiral-stent longer and simultaneously reduce its diameter thereby increases also the space between the inflated balloon and the spiral-stent. Both motions are advantageous for removing the stent device with a sheath. The anti-force to the pulling of the threads can be executed by the inflated balloon. The threads at the upper end of the stent can also preferably be extended and integrated with the balloon (see also FIG. 7).

Marker(s) 12 may be provided on the delivery sheath, visible e.g. fluoroscopic control to ensure perfect position. Further, there may be marker(s) 33 at the top and bottom of the tubular part of the supporting stent that are visible with e.g. fluoroscopic control to ensure perfect position. There may also be marker(s) 34 between the markers at the top and bottom of the tubular part of the stent. These middle markers can e.g. be located at a distance from the top of the spiral-stent, which is equal to the length of the balloon. The size of the spiral-stent is preferably of a diameter sized so that the blood pressure will be significantly higher above the device than below it. This fact in itself implies priority of the blood support to the upper organs in the body. This is obtained by having a diameter of the expanded stent being smaller than the diameter of the artery where it is placed.

The supporting stent is preferably only connected to the balloon at its top, where it can be intergraded to the upper surface of the balloon to facilitate removal (FIG. 7).

An example of how the kit and stent device can be used will now be discussed in more detail, with reference to FIGS. 2-7.

In this example, the stent device is arranged to temporarily cover the rupture of the aorta, whereby the central channel with the supporting stent ensures blood flow to both legs. However, it is to be acknowledged by someone skilled in the art that the stent device and kit of the present invention may also be used in a similar manner for treating other types of aneurysms.

In a first step, a puncture is made into a femoral artery (FIG. 2), and a guide wire is inserted into the artery, and through the aneurysm. Typically, the main side (usually the right side) is used for introducing the guide wire, for positioning it in the thoracic aorta. This procedure is per se known in the art.

Figure 4:
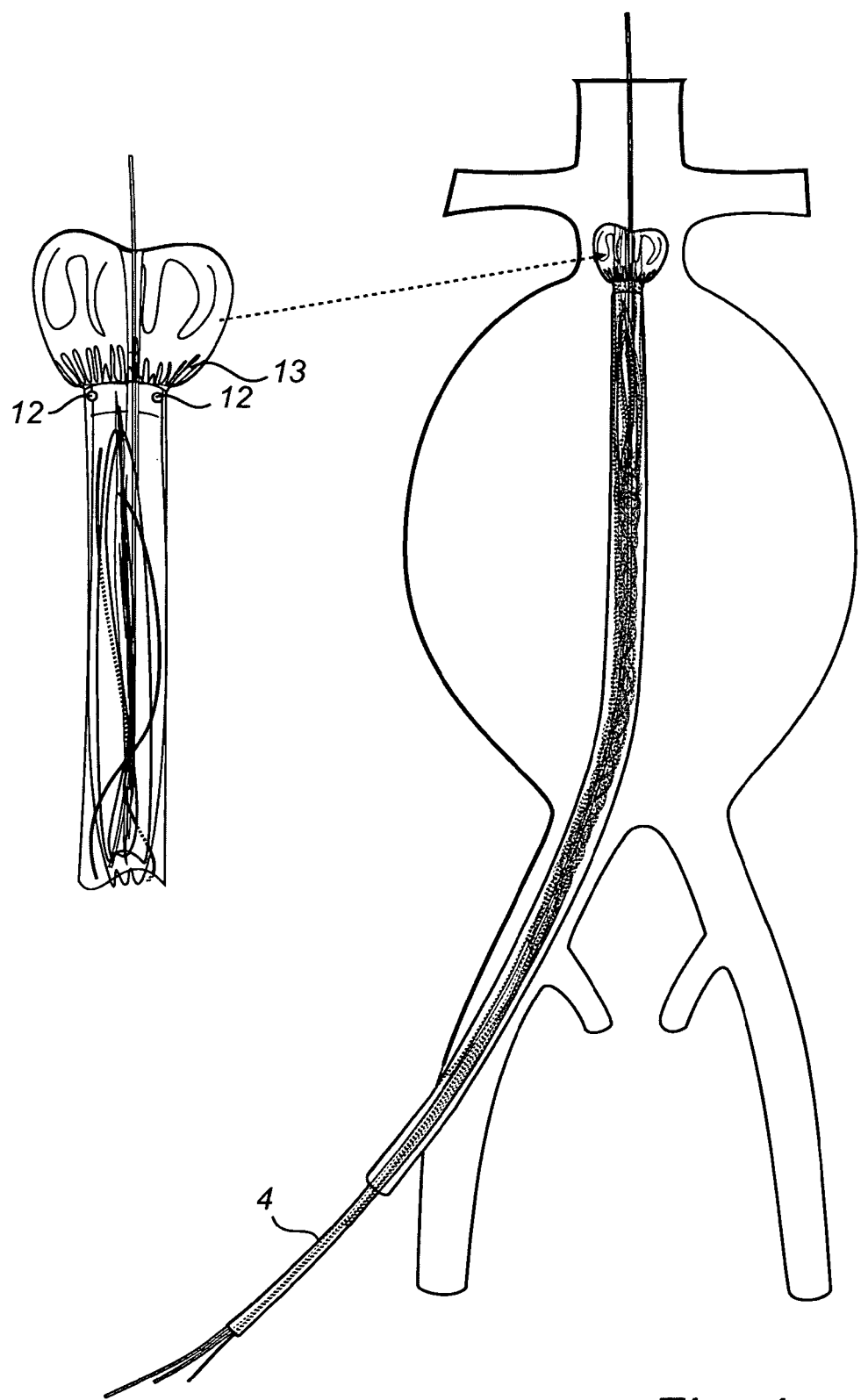

The kit as discussed in the foregoing is then inserted, following the guide wire, through the femoral artery in the groins as an endovascular procedure (FIG. 3), and up to the intended position in the aneurysm in the aorta (FIG. 4). The position is controlled by the marks at the top and bottom of the spiral-stent and by the marks at the top of the delivery sheath. The lower end should preferably be in the iliac artery.

Figure 5:
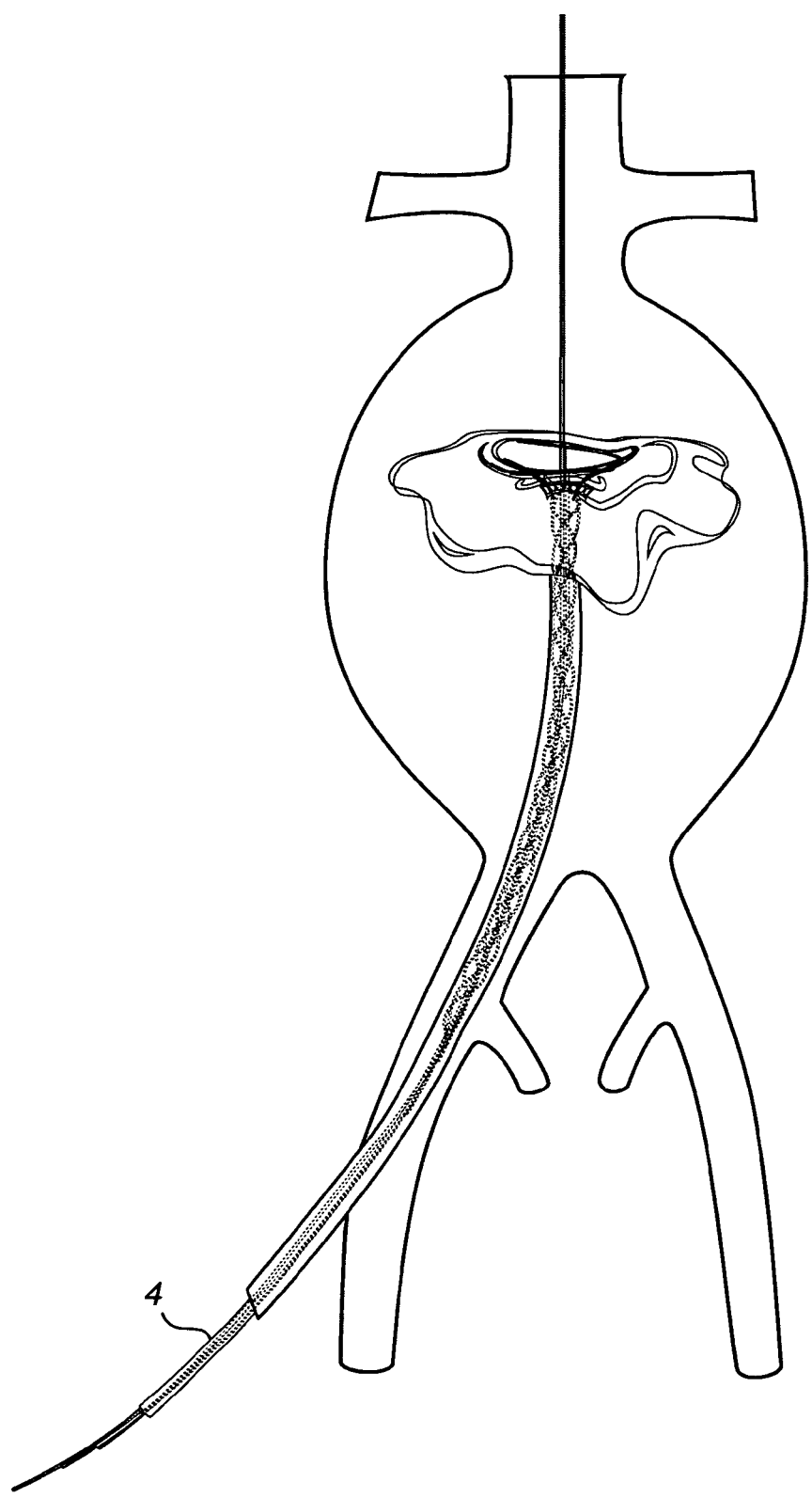
Figure 6:
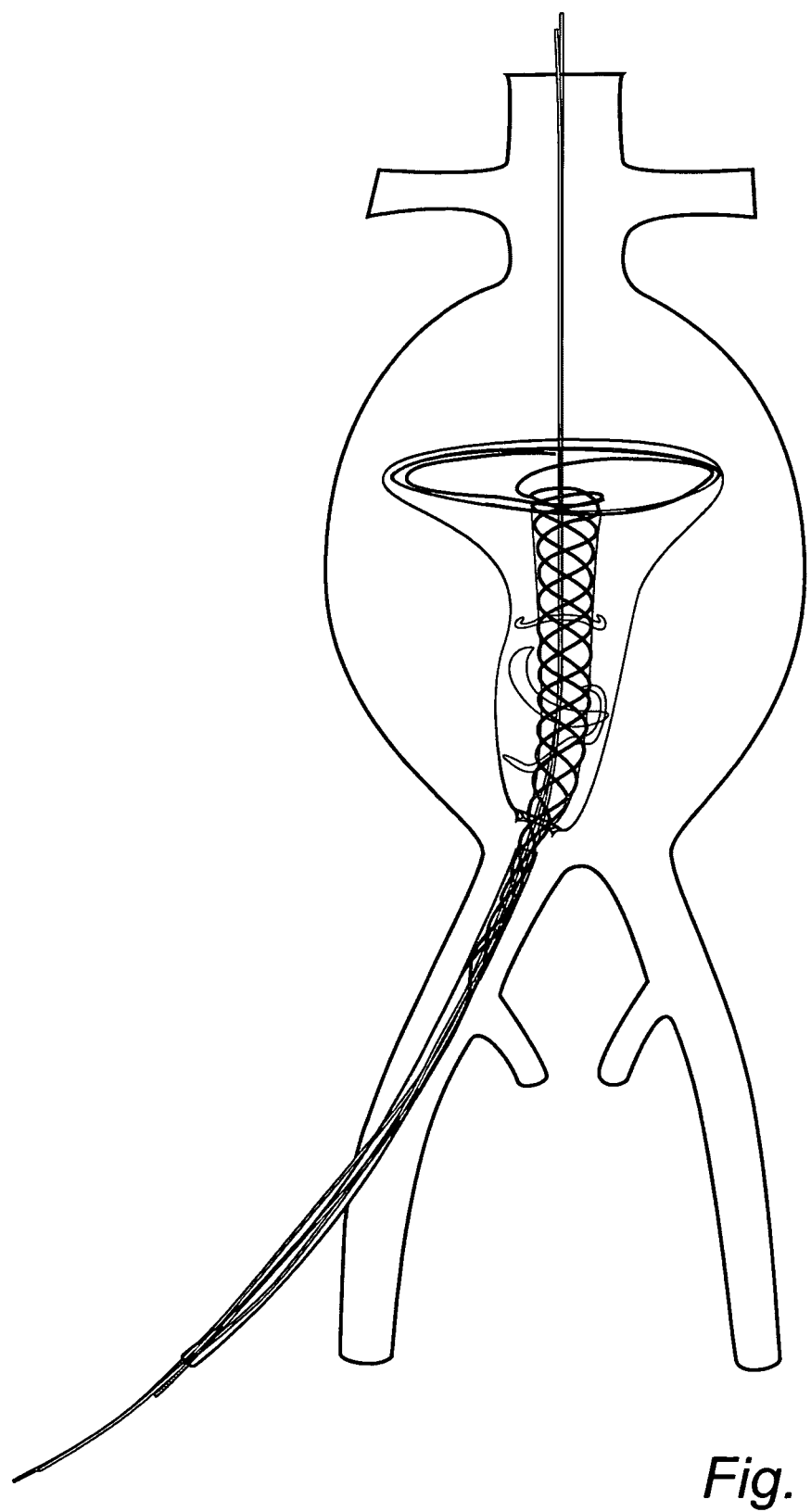

In this position, the delivery sheath is pulled downwards (FIG. 5). This force is counteracted by the pushing rod 4.

The position is preferably secured when the balloon has left the delivery sheath which is when the upper end of the spiral-stent is at the tip of the delivery sheath. This can be identified when the markers at the top of the delivery sheath and the top of the spiral-stent are at the same level. The upper and the middle markers on the spiral-stent are hereby in the aorta. The balloon is fully everted when the tip of the delivery sheath is at the level of the middle marker on the spiral-stent.

The everted balloon is now inflated. The balloon should preferably first be partly inflated, and preferably with a solution which can be identified under fluoroscopic vision. Then, the balloon may, if necessary be pulled downwards so the balloon touches the bottom of the aneurysm. This might be achieved automatically by the blood pressure on the top of the balloon. The balloon is then fully inflated (FIG. 7) so that it essentially fills the aneurysm. Inflation of the balloon is made under control of the inflation pressure, until it touches the side-walls of the aorta.

Subsequently, the delivery sheath is disconnected from the balloon. If the connection between the delivery sheath and the balloon is based on different strengths between pulling and twisting forces, the delivery sheath should hereby be twisted to release the balloon from its connection to the delivery sheath. Then, the delivery sheath may be pulled out.

Figure 8:
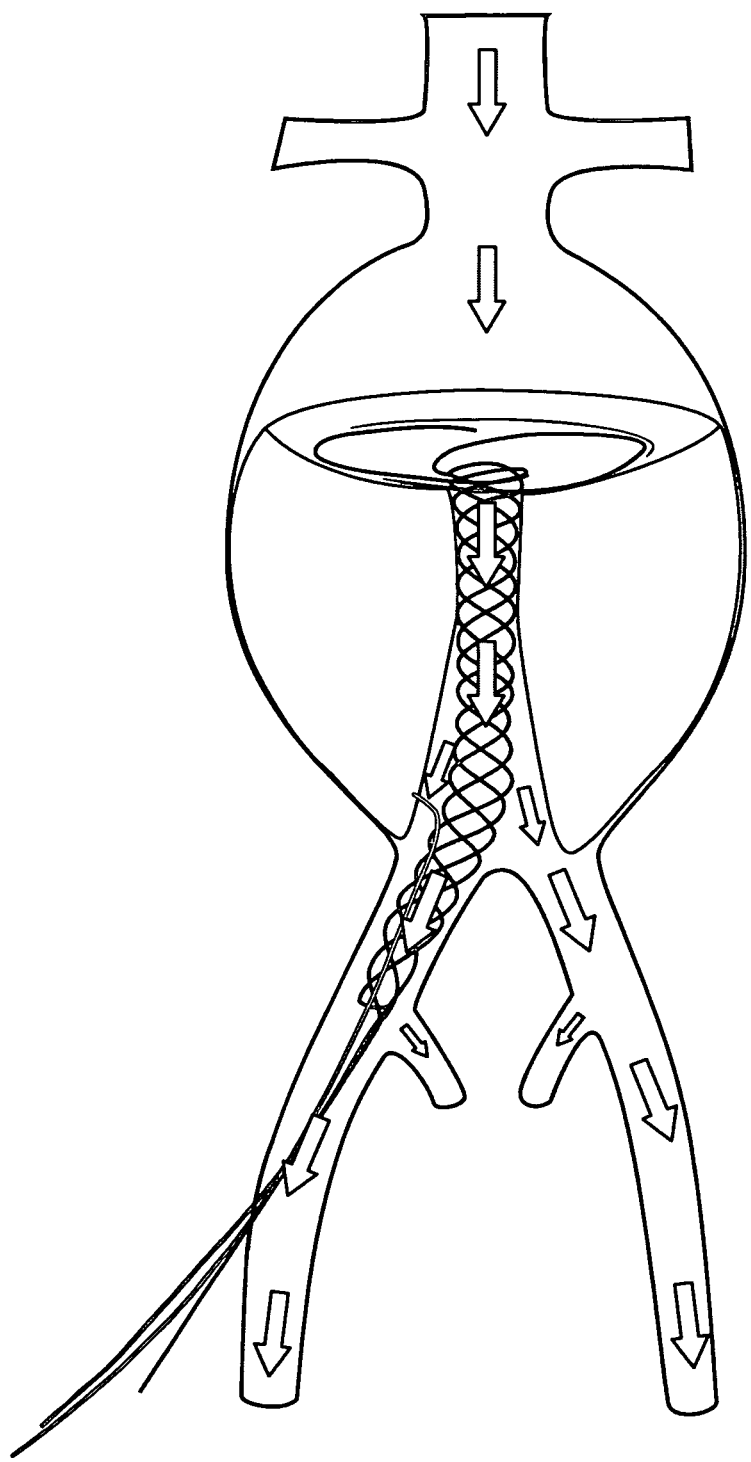
FIG. 8 illustrate the stent device of FIG. 1 in an operative disposition.

The stent device is now in an operative position (FIG. 8). Externally the stent device is still controllable by means of the thin tubing to inflate the balloon and the control ends of the spiral-stent. The supporting stent may extend into one of the iliac arteries to secure the position of the stent device in relation to the arteries to the legs. The result may be constantly verified with fluoroscopy and with radio-opaque dye from the left side. In this disposition, the aneurysm is temporarily treated, and sufficient blood flow is obtained through the stent device.

Figure 9:
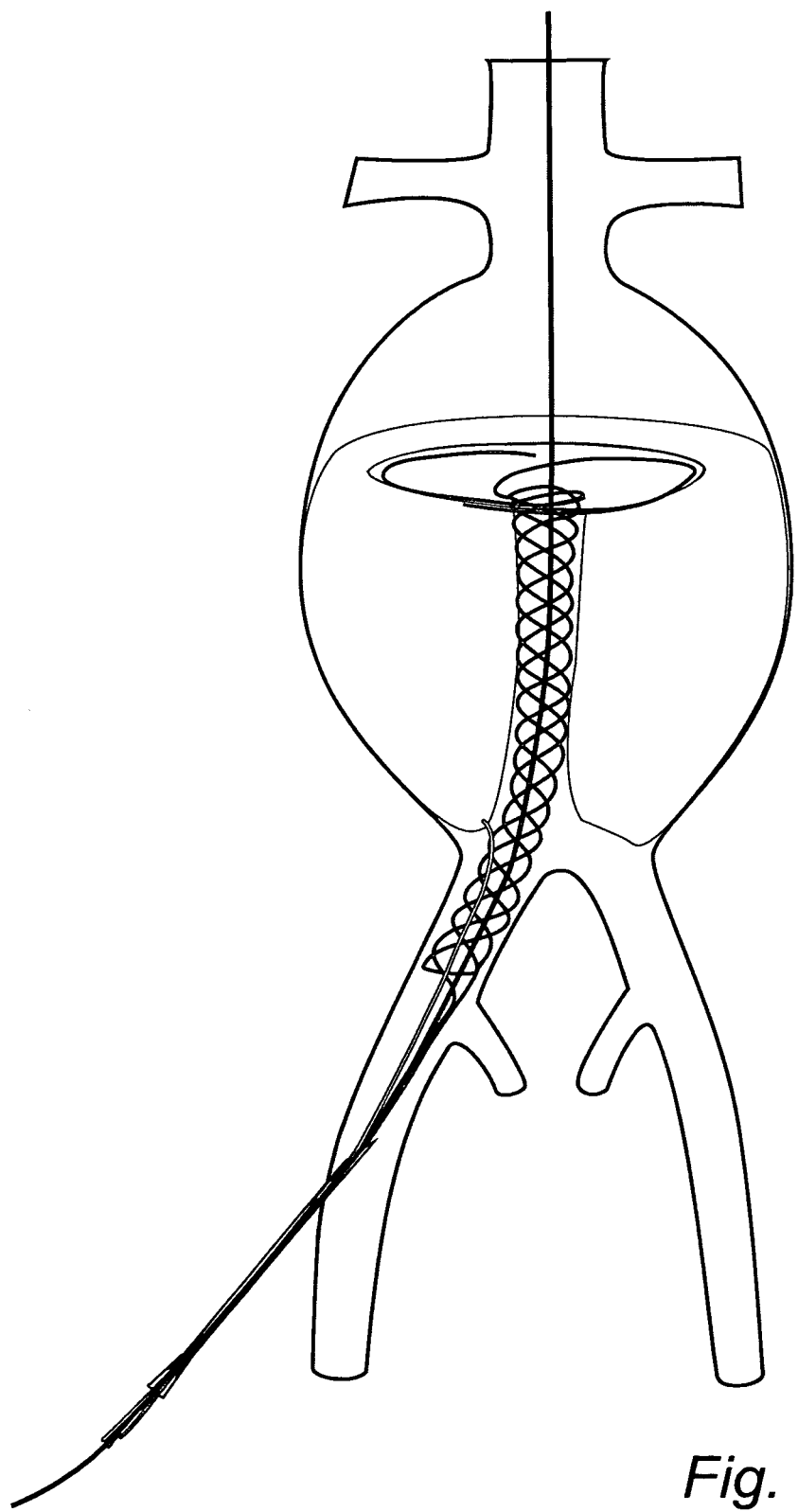
FIGS. 9-11 illustrate different steps when removing the stent device of FIG. 1.

When it is decided to be clinically appropriate to remove the stent device, both femoral arteries in the groins may be punctured. The externally placed threads of the stent can be placed within the lumen of the punctating needle. Thereafter, a guide wire may again be arranged through the aneurysm (FIG. 9), and an extraction or docking sheath 5 may be introduced from the right side and be positioned in the lower part of the iliac arteries, below the spiral-stent. The docking sheath preferably has marks at its tip that can be identified.

The external control ends, i.e. the extension from the spiral-stent, may then be pulled. The force will be counteracted by the balloon. Hereby, the spiral-stent gets a big reduction in diameter.

Figure 10:
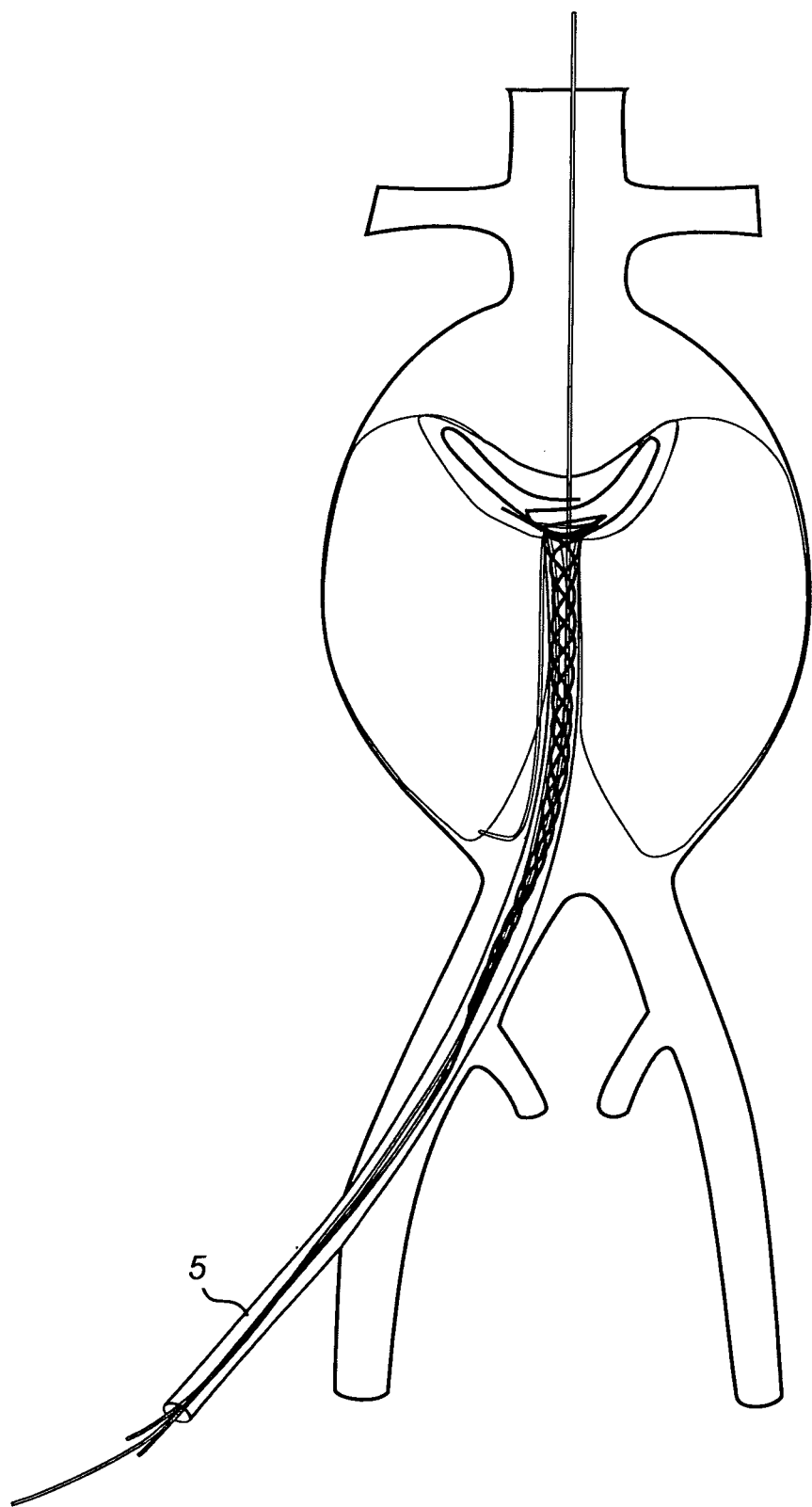

The docking sheath 5 is then inserted over the whole spiral-stent (FIG. 10). This may be identified when the tip of the docking sheath is at the same level as the top of the spiral-stent. The balloon may then be deflated.

Figure 11:
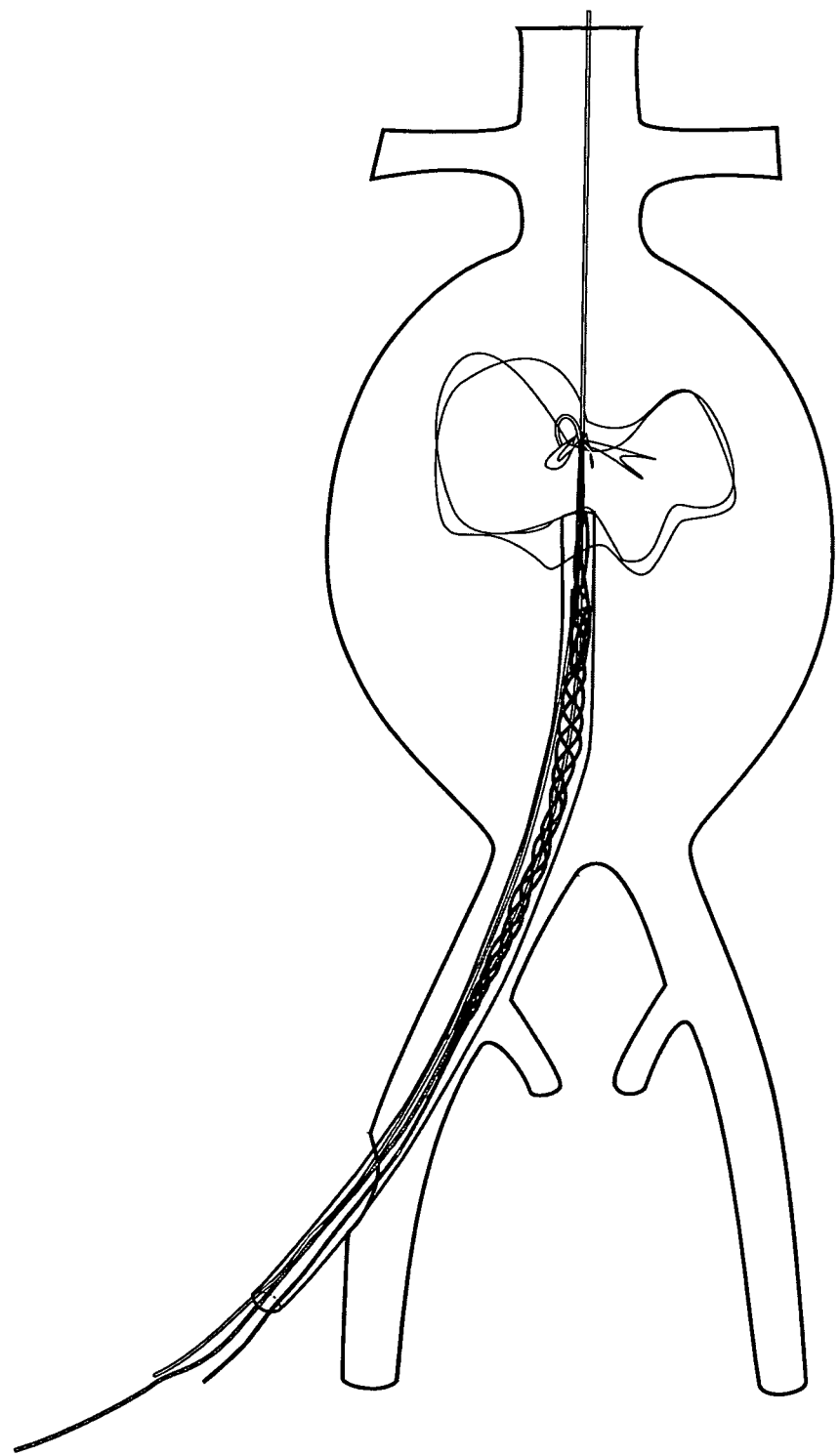

Further pulling of the control ends will then pull the upper surface of the balloon into the docking sheath (FIG. 11).

When the balloon is completely pulled into the docking sheath, the docking sheath may be removed with the stent device inside.

In the case of a ruptured aortic aneurysm both femoral arteries in the groins may be punctured. The opposite side to the one where the stent device is inserted can then be a back-up in case of a sudden drop of blood pressure. In such a situation proximal control can be reached with an occluding balloon from that alternative side (usually the left side).

The inflation of the expandable balloon may also be controlled in accordance with the pressure in the balloon. For example, the tubing used to inflate/deflate the expandable balloon may be connected to a pressure gauge. Hereby, the pressure may be monitored, for control of the inflation process during insertion of the stent device. Additionally or alternatively, the pressure sensor may also be used to continuously control the expansion of the balloon when it is in the operative position, as well as during deflation for removal of the stent device. Specifically, the inflation may be controlled in dependence of the pressure variation that occurs during each heart beat. Hereby, it is possible to provide an efficient control of the inflation in order to obtain both adequate closure of the aneurysm and sufficient blood flow through the stent device.

Notably, both the above-discussed balloon and the above-discussed supporting stent are useable separately.

For example, the balloon may function without the spiral-stent since the balloon itself has a channel and the balloon will cover the rupture. The advantage with a spiral-stent present is that the flow of blood to the legs is more secure through the central part of the balloon. Furthermore, the lower opening of the balloon will be better positioned in relation to the iliac arteries to the legs and the shape of the upper surface of the balloon supported. However, the balloon may be used as a stent device without any supporting stent. For example, a torus shaped balloon can fill a cavity but still have an open channel, which can be further supported by a locally less elastic material. This would put an artificial wall against the leaking aneurysm. The advantage for such a device would e.g. be a thinner introducer sheath.

Further, the supporting stent discussed above, and in particular the spiral-stent embodiment, provides a spiral shaped tubular vessel that has the properties that it has permeable walls and that its cross-sectional area can be altered given the tension in the filaments or threads defines its diameter. The realizations of such a tube include two or several spirals curled interfoliated in different direction. The possibility to remove the described spiral-stent is highly advantageous, since prior known stents will all remain in place permanently. This characteristic is of value in conditions where only a temporary dilatation or outwards pressure is needed. An example is aortic dissection. In this disease the aortic wall is split longitudinally giving rise to a double-barrel conduit. The aim of the treatment is to close the false pipe. It can be achieved by pressing the membrane separating the false and true lumen towards the aortic wall. The stent has to be placed in the true lumen. In many occasions the membrane is present in connection to crucial arteries (celiac trunk, superior mesenteric artery, renal arteries, arteries to the spinal cord). With today's available therapy clinicians hesitate to apply stents, which will be present indefinitely in such areas. It is known that the separating membrane will adhere to the aortic wall again after a period of healing, in case that these tissues get in touch. A solution to the problem would be to apply the above-discussed spiral-stent until such a healing has occurred and then remove it again. An anti-force can be applied if such an alternative stent has its threads forming the spirals extended into standard straight configurations at both ends. The threads at one end can thereby be snared and the threads at the other end pulled.

A number of variations of the stent device and the kit are feasible. This description is only one example to give insights to principles of delivery, function and removal of the stent device. For example, it is possible to use permeable supporting stents formed of net-like walls or the like, or walls provided with a plurality of perforations to provide adequate permeability. Further, the balloon may, in the insertion disposition, be arranged in other ways than in line with the supporting stent, such as within the supporting stent, or outside the supporting stent. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A stent device for treating an aneurysm comprising:
   an expandable balloon with a channel extending through said expandable balloon from one side to another; and
   a supporting stent connected to said expandable balloon,
   wherein the supporting stent is, in an operative disposition, arranged at least partly within said channel of said expandable balloon when said expandable balloon is expanded,
   wherein said supporting stent has walls which are permeable to blood,
   wherein the expandable balloon is connected to the supporting stent only at or adjacent to a proximal end of said supporting stent, and
   wherein the expandable balloon, in an insertion disposition, is arranged within the supporting stent, and the expandable balloon is eversible into an expanded state outside said supporting stent in the operative disposition.

2. The stent device of claim 1, wherein a relative position between the expandable balloon and the supporting stent in an axial direction of the stent device is variable, and
   wherein in the insertion disposition, the expandable balloon and the supporting stent are arranged in line with each other.

3. The stent device of claim 1, wherein the channel of the expandable balloon is arranged in a center of the expandable balloon when the expandable balloon has a torus shape in the expanded state.

4. The stent device of claim 1, wherein the supporting stent has a variable diameter, said diameter being remotely controllable.

5. The stent device of claim 1, wherein the supporting stent is self-expandable, and automatically strives to resume an expanded state after being released from a compressed state.

6. The stent device of claim 1, wherein the supporting stent is formed of threads arranged in at least two interfoliated spirals.

7. The stent device of claim 6, wherein ends of the threads forming the at least two interfoliated spirals extend beyond the supporting stent, whereby a diameter of the supporting stent is remotely controllable by varying tension of the extending ends of the threads.

8. The stent device of claim 1, wherein a diameter of the supporting stent in the operative disposition is less than 2 cm.

9. A kit for treating an aneurysm, comprising:
   a delivery sheath; and
   a stent device according to claim 1, wherein the delivery sheath releasably accommodates the stent device.

10. The kit of claim 9, wherein the expandable balloon, in the insertion disposition, is connected to the supporting stent at one end and to the delivery sheath at an opposite end.

11. The kit of claim 10, wherein the connection between the expandable balloon and the delivery sheath is releasable.

12. The kit of claim 9, wherein at least one of the stent device and the delivery sheath comprises markers visible by external observation.

13. The kit of claim 9, further comprising an extraction sheath for removal of the stent device from the aneurysm.

14. The kit of claim 12, wherein the markers are visible, by fluoroscopic vision.

15. A method for treating an aneurysm, comprising:
   inserting the kit according to claim 9 into the aneurysm;
   pulling back the delivery sheath, thereby releasing the stent device; and
   expanding the expandable balloon in the aneurysm, wherein a fluid communication through the aneurysm is created through the channel in the expandable balloon.

* * * * *